(12) United States Patent
Bresolin et al.

(10) Patent No.: US 8,345,989 B1
(45) Date of Patent: Jan. 1, 2013

(54) ILLUMINATION STATION FOR USE IN PHARMACEUTICAL IDENTIFICATION SYSTEM AND METHODS THEREFOR

(75) Inventors: Stefano Bresolin, Durham, NC (US); David Newcomb, Morrisville, NC (US); Christopher E. Paul, Hillsborough, NC (US); Pete Klein, Durham, NC (US); Caelan Klein, legal representative, Williamsburg, MI (US)

(73) Assignee: Parata Systems, LLC, Durham, NC (US)

( * ) Notice: Subject to any disclaimer, the term of this patent is extended or adjusted under 35 U.S.C. 154(b) by 481 days.

(21) Appl. No.: 12/703,400

(22) Filed: Feb. 10, 2010

Related U.S. Application Data (60) Provisional application No. 61/152,836, filed on Feb. 16, 2009.

(51) Int. Cl.
*G06K 9/68* (2006.01)
*G06K 9/00* (2006.01)

(52) U.S. Cl. ..................................................... 382/218

(58) Field of Classification Search .................. 382/143, 382/162, 164, 165, 218–220; 356/73, 301; 424/490; 348/125, E07.085
See application file for complete search history.

(56) References Cited

U.S. PATENT DOCUMENTS

| | | | |
|---|---|---|---|
| 5,206,030 A * | 4/1993 | Wheatley et al. | 424/490 |
| 6,310,686 B1 | 10/2001 | Jiang | |
| 6,373,567 B1 | 4/2002 | Wise et al. | |
| 6,535,637 B1 | 3/2003 | Wootton et al. | |
| 6,542,238 B1 | 4/2003 | Tsuboi et al. | |
| 6,771,369 B2 | 8/2004 | Rzasa et al. | |
| 7,028,723 B1 | 4/2006 | Alouani et al. | |
| 7,218,395 B2 | 5/2007 | Kaye et al. | |
| 7,889,330 B2 * | 2/2011 | Newcomb | 356/73 |
| 2004/0183237 A1 | 9/2004 | McGrath et al. | |
| 2004/0263843 A1 | 12/2004 | Knopp et al. | |
| 2005/0134856 A1 | 6/2005 | Rutledge | |
| 2005/0220335 A1 | 10/2005 | Budd | |
| 2005/0248759 A1 | 11/2005 | Wang et al. | |
| 2007/0008523 A1 | 1/2007 | Kaye et al. | |
| 2007/0042346 A1 | 2/2007 | Weller | |

(Continued)

FOREIGN PATENT DOCUMENTS

CN 101118363 A 6/2008

(Continued)

OTHER PUBLICATIONS

The International Search Report and the Written Opinion for International Application No. PCT/US2009/057383, mailed Dec. 7, 2009.

(Continued)

*Primary Examiner* — Amir Alavi
(74) *Attorney, Agent, or Firm* — Myers Bigel Sibley & Sajovec (57) ABSTRACT

A method of determining the identity of pharmaceutical tablets contained within a pharmaceutical vial includes the steps of: obtaining a first image of the vial as it is illuminated with colored light; obtaining a second image of the vial as it is illuminated with infrared radiation; processing the first and second images to obtain comprehensive image data; comparing the comprehensive image data to image data of a known pharmaceutical expected to be contained in the vial; and determining whether the pharmaceutical in the vial is the expected pharmaceutical based on the comparing step. The use of images obtained under both colored and IR illumination can assist in producing an accurate comprehensive image data.

13 Claims, 9 Drawing Sheets

U.S. PATENT DOCUMENTS

| | | |
|---|---|---|
| 2008/0183410 A1 | 7/2008 | Klein et al. |
| 2010/0128165 A1 | 5/2010 | Newcomb et al. |
| 2011/0096998 A1* | 4/2011 | Newcomb ............... 382/218 |
| 2011/0170764 A1* | 7/2011 | Bresolin ............... 382/143 |
| 2012/0013734 A1* | 1/2012 | Ranieri et al. ............ 348/125 |

FOREIGN PATENT DOCUMENTS

| | | |
|---|---|---|
| DE | 11 17 046 B | 11/1961 |
| DE | 11 80 317 B | 10/1964 |
| DE | 195 01 650 A1 | 7/1996 |
| DE | 10 2004 016 829 A1 | 11/2005 |
| EP | 1 003 027 A1 | 5/2000 |
| FR | 2 726 651 A1 | 5/1996 |
| JP | 03 214045 A | 9/1991 |
| JP | 2004 226071 A | 8/2004 |
| WO | WO 97-48329 | 12/1997 |
| WO | WO 02-25568 A1 | 3/2002 |
| WO | WO 2006-036434 | 4/2006 |

OTHER PUBLICATIONS

The International Search Report and the Written Opinion for PCT/US2009/064608, mailed May 3, 2010.

The International Search Report, mailed Jun. 25, 2008, for corresponding application PCT-US2008-000387.

Partial International Search Report for PCT/US2009/065617, mailed Jun. 4, 2010.

* cited by examiner

ILLUMINATION STATION FOR USE IN PHARMACEUTICAL IDENTIFICATION SYSTEM AND METHODS THEREFOR

RELATED APPLICATION

The present application claims priority from U.S. Provisional Patent Application No. 61/152,836, filed Feb. 16, 2009, the disclosure of which is hereby incorporated herein in its entirety.

FIELD OF THE INVENTION

The present invention is directed generally to imaging, and more particularly to imaging and processing of images of objects residing within a container.

BACKGROUND OF THE INVENTION

There is an ongoing and predicted long-term shortage of licensed pharmacists. Due to the increasing age of the population and the ever-increasing number of prescription medicines available, the demand for prescription drugs is growing at a rate that will far exceed the capacity and numbers of licensed pharmacists. The net impact of this imbalance is that pharmacists are increasingly spending more time doing clerical and administrative tasks such as verifying filled prescriptions and checking data entry done by pharmacy technicians. Since the capacity of any one pharmacist is fixed, the output of a pharmacy has become constrained. Consequently, the labor and total cost per prescription continues to rise. The December 2000 Department of Health and Human Services Report to Congress titled "The Pharmacist Workforce: A Study of the Supply and Demand for Pharmacists", which is hereby incorporated by reference into the present application, provides an overview of the above problem.

Due to these increased demands on a pharmacist's time, and the resulting increased reliance on technicians and other non-professional staff to fill prescriptions, there is an increased chance for prescription error. While these errors may take many forms, the likelihood of a dangerous or life threatening "adverse drug event" increases proportionally with the increased chance of prescription fill error. Several studies have shown that prescription error rates are consistently in the 2% to 7% range, with a 4% error rate often cited as a reliable average. The number of deaths due to medication errors is estimated to exceed 7,000 per year in the United States alone. Of course, this number does not include non-fatal conditions from drugs that also result in some form of trauma or injury. The resulting litigation costs associated with these prescription fill errors have also dramatically increased.

Many existing pharmacy filling systems and procedures still require a human operator, whether that operator is a technician or a licensed pharmacist, to validate visually whether the drug that is delivered to the customer is correct. Thus, the human factor can contribute to the majority of prescription fill errors. Existing visual verification techniques typically rely on comparing an electronic image of the prescribed medication, i.e., a picture of the prescribed medication retrieved from a data library, with the actual medication that is dispensed for the patient. Other systems and procedures rely on comparing the dispensed medication with that in the original manufacturer's supply container, or comparing an electronic image of the filled prescription with an electronic image of the prescribed medication retrieved from a data library.

Each of these verification systems presents similar problems. First, these known verification methods assume that all drugs are visually distinct. This assumption causes many problems because many drugs are not, in fact, visually distinct and, in other cases, the visual differences between drugs is very subtle. For instance, manufacturers are rapidly running out of unique shapes, colors and sizes for their solid dosage form products. To further complicate the problem, generic drug manufactures may be using shapes, colors, and sizes that are different than that of the original manufacturer. Second, even though some known systems may utilize a National Drug Code (NDC) bar code to verify that the supply bottle being accessed corresponds correctly to the patient's prescription, a fraction of filled prescriptions that are never picked up are returned to the supply shelves for reuse in later prescriptions. These reused bottles will not, therefore, have a manufacturer's bar code on them. It is difficult, if not impossible, to incorporate such validation schemes for these unused prescriptions. Furthermore, in these circumstances, a supply bottle is not available for a visual comparison with the filled prescription. Finally, each of these known manual verification and validation techniques typically requires that the pharmacist spend a significant portion of his day performing these administrative or clerical tasks and allows less time for patient consultation and other professional pharmacist activities.

Solid dosage pharmaceuticals (e.g. pills, tablets, and capsules) each have a unique chemical composition associated with them. This is often referred to as a chemical signature or fingerprint. Pharmaceuticals with varying dosage levels of the same active ingredient may have unique chemical signatures as well. Even slight variations in the active ingredient typically produce a unique chemical signature. In that regard, most pharmaceuticals can be identified accurately by the use of some form of chemical analysis. This same methodology may be applied to other forms of medication (e.g. liquids, creams, and powders). Particularly with solid dosage pharmaceutical products, while a group or package of products may look identical in the visible portion of the spectrum each product may have a unique chemical signature in the near-infrared wavelength range (800 to 2500 nm). For example, U.S. Pat. No. 6,771,369 to Rzasa et al. describes a pharmaceutical discrimination system that relies on NIR for scanning the contents of a pharmaceutical vial. As another example, U.S. Pat. No. 7,218,395 to Kaye et al. describes the use of Raman spectroscopy for scanning vial contents. U.S. Patent Publication No. 20080183410 describes another spectroscopy-based discrimination system that can analyze pharmaceuticals as they are present in a capped pharmaceutical vial.

Although these spectroscopy systems can be very accurate, in many instances it may be necessary or helpful to verify the identity of the pharmaceutical visually. Naturally, if the pharmaceutical has already been dispensed into a vial, removal from the vial (or even uncapping of the vial) can slow the dispensing process. However, it is common for pharmaceutical vials to be largely transparent and have an amber color. The use of amber-colored vials began as an attempt to preserve the potency of the pharmaceuticals contained therein (based on the belief that amber coloration helped to prevent the passage of UV radiation, which might damage the pharmaceuticals), and their use has continued as a matter of convention. Thus, the use of a conventional vision system to verify the contents of a vial visually is difficult, because often the color of the pharmaceutical is one of its most distinguishing characteristics, and the amber color of the vial can adversely affect the accuracy of the color presented to the vision system.

One solution to color identification and verification is discussed in U.S. patent application Ser. No. 12/249,402, filed on Oct. 10, 2008, the disclosure of which is hereby incorporated herein in its entirety. This system includes an analysis chamber camera assembly that can capture an image of medication pills through the bottom surface of an amber or other color transparent vial. The system includes a bowl shaped chamber into which light is dispersed. A window at the "base" of the bowl allows light to reach the bottom surface of the vial. The shape of the chamber can minimize reflections on the chamber window. The use of an anti-glare coating on the chamber window can also contribute to keeping light glare/reflection at a minimum. An LED light ring is used to evenly disperse the light throughout the bowl chamber. A light curtain is used to block direct light from the LEDs to further assist in reducing light glare/reflection. Certain surfaces may be painted white where light is channeled for efficiency, and others may be painted black to eliminate glare.

The LED light ring includes multiple sets of LEDs, alternated and symmetrically arranged along the light ring's edge to provide uniform illumination such that light intensity from a given wavelength is balanced in each direction. The color of the light from the LEDs mounted on the ring may be monochromatic in the visible range (e.g. red, green, blue) and may be adjusted to "cancel" the color of the vial. The structure of the light ring is discussed in U.S. patent application Ser. No. 12/623,878, filed Nov. 23, 2009, the disclosure of which is hereby incorporated herein in its entirety.

The ring is configured to allow independent control of the light intensity of the different colors. The ring can also be set up so that the intensity of all the colors can be changed together, but equally balanced. This design can allow automatic color adjustment of a vial type of any color of transparent material.

Although this system may provide versatility, imaging techniques may still be improved for certain drugs, vials, or combinations thereof.

SUMMARY OF THE INVENTION

As a first aspect, embodiments of the invention are directed to a method of determining the identity of pharmaceutical tablets contained within a pharmaceutical vial. The method comprises the steps of: obtaining a first image of the vial as it is illuminated with colored light; obtaining a second image of the vial as it is illuminated with infrared radiation; processing the first and second images to obtain comprehensive image data; comparing the comprehensive image data to image data of a known pharmaceutical expected to be contained in the vial; and determining whether the pharmaceutical in the vial is the expected pharmaceutical based on the comparing step. The use of images obtained under both colored and IR illumination can assist in producing accurate comprehensive image data.

As a second aspect, embodiments of the invention are directed to a method of determining the identity of pharmaceutical tablets contained within a pharmaceutical vial, comprising the steps of: obtaining a first image of the vial as it is illuminated with colored light; obtaining a second image of the vial as it is illuminated with infrared radiation; obtaining a third image of the vial as it is illuminated with light of a color that is a different color than the light employed in obtaining the first image; processing the first, second and third images to obtain comprehensive image data; comparing the comprehensive image data to image data of a known pharmaceutical expected to be contained in the vial; and determining whether the pharmaceutical in the vial is the expected pharmaceutical tablets based on the comparing step.

As a third aspect, embodiments of the invention are directed to an imaging system, comprising: an imaging chamber; an imaging device positioned to acquire an image of a container residing in the imaging chamber; and a light source position to illuminate a container residing in the imaging chamber, the light source including a source of colored, visible light and a source of infrared light.

As a fourth aspect, embodiments of the invention are directed to a method of determining the identity of pharmaceutical tablets contained within a pharmaceutical vial, comprising the steps of: obtaining a first image of the vial as it is illuminated with light selected to identify features of the vial; obtaining a second image of the vial as it is illuminated with light selected to identify regions that contain tablets; obtaining a third image of the vial as it is illuminated with light that is selected to provide color information about the tablets; processing the first, second and third images to obtain comprehensive image data; comparing the comprehensive image data to image data of a known pharmaceutical expected to be contained in the vial; and determining whether the pharmaceutical in the vial is the expected pharmaceutical based in the comparing step.

As a fifth aspect, embodiments of the invention are directed to a method of determining the identity of pharmaceutical tablets contained within a pharmaceutical vial, comprising the steps of: obtaining a first image of the vial as it is illuminated with light selected to identify features of the vial and to provide color information about the tablets; obtaining a second image of the vial as it is illuminated with light selected to identify regions that contain tablets; processing the first and second images to obtain comprehensive image data; comparing the comprehensive image data to image data of a known pharmaceutical expected to be contained in the vial; and determining whether the pharmaceutical in the vial is the expected pharmaceutical based on the comparing step.

DETAILED DESCRIPTION OF EMBODIMENTS OF THE INVENTION

The present invention will now be described more fully hereinafter, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art. In the drawings, like numbers refer to like elements throughout. Thicknesses and dimensions of some components may be exaggerated for clarity.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein the expression "and/or" includes any and all combinations of one or more of the associated listed items.

In addition, spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly.

Well-known functions or constructions may not be described in detail for brevity and/or clarity.

Figure 1:
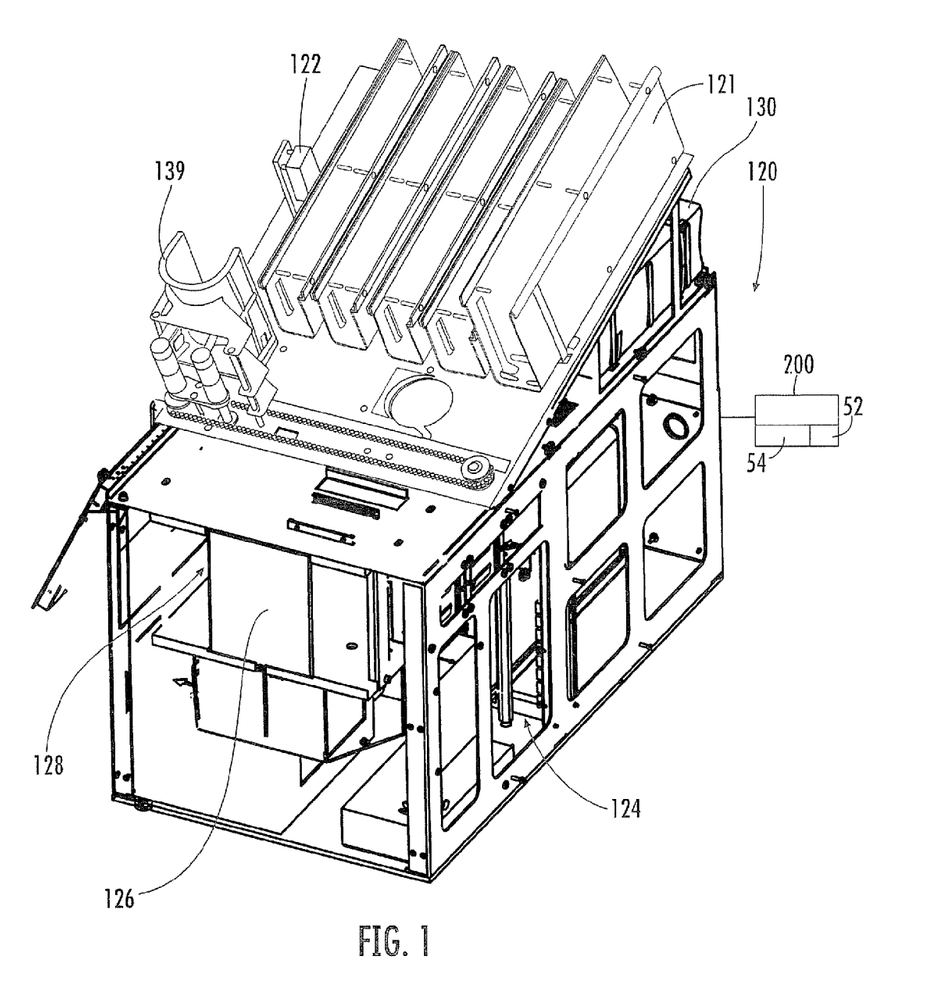
FIG. 1 is a perspective view of a system suitable for performing methods according to embodiments of the present invention.

Turning now to the figures, FIG. 1 illustrates a pharmaceutical verification system 120 according to embodiments of the present invention. The system 120 includes a vial loading station 121, bar code scanning or RFID reading station 122, a vision station 124, a spectroscopy station 126, a stamping station 128, and an offload station located underneath the vial loading station 121 (not visible in FIG. 1). Vials are moved between these stations with a sliding conveyor 139 adjacent the bar code scanning station and a wheel conveyor (not shown). A controller 200 controls the operation of the various stations and the conveyor. The operation of the system 120 is described in greater detail in co-pending and co-assigned U.S. Provisional Patent Application Ser. No. 61/118,006, filed Nov. 26, 2008, and U.S. patent application Ser. No. 12/623,917, filed Nov. 23, 2009, the disclosure of each of which is hereby incorporated herein in its entirety.

Figure 2:
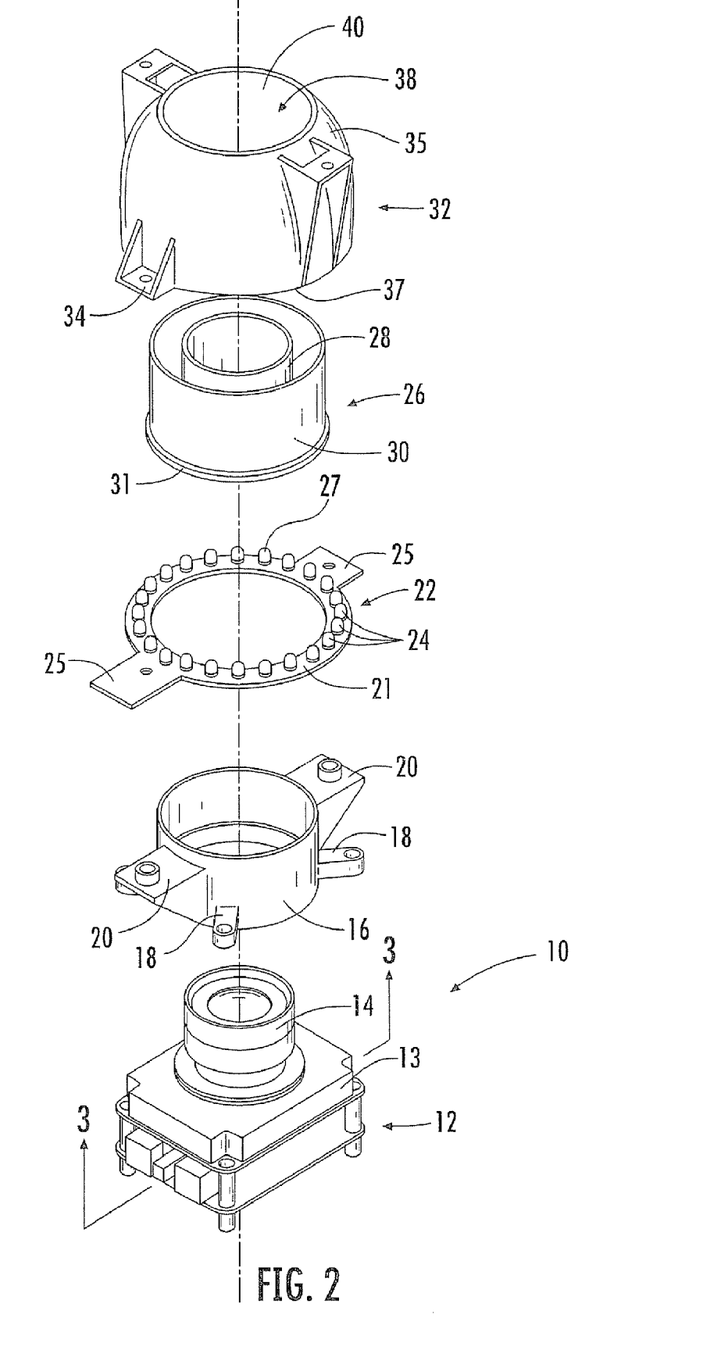
FIG. 2 is an exploded perspective view of components of a vision system include in the overall system of FIG. 1.
Figure 3:
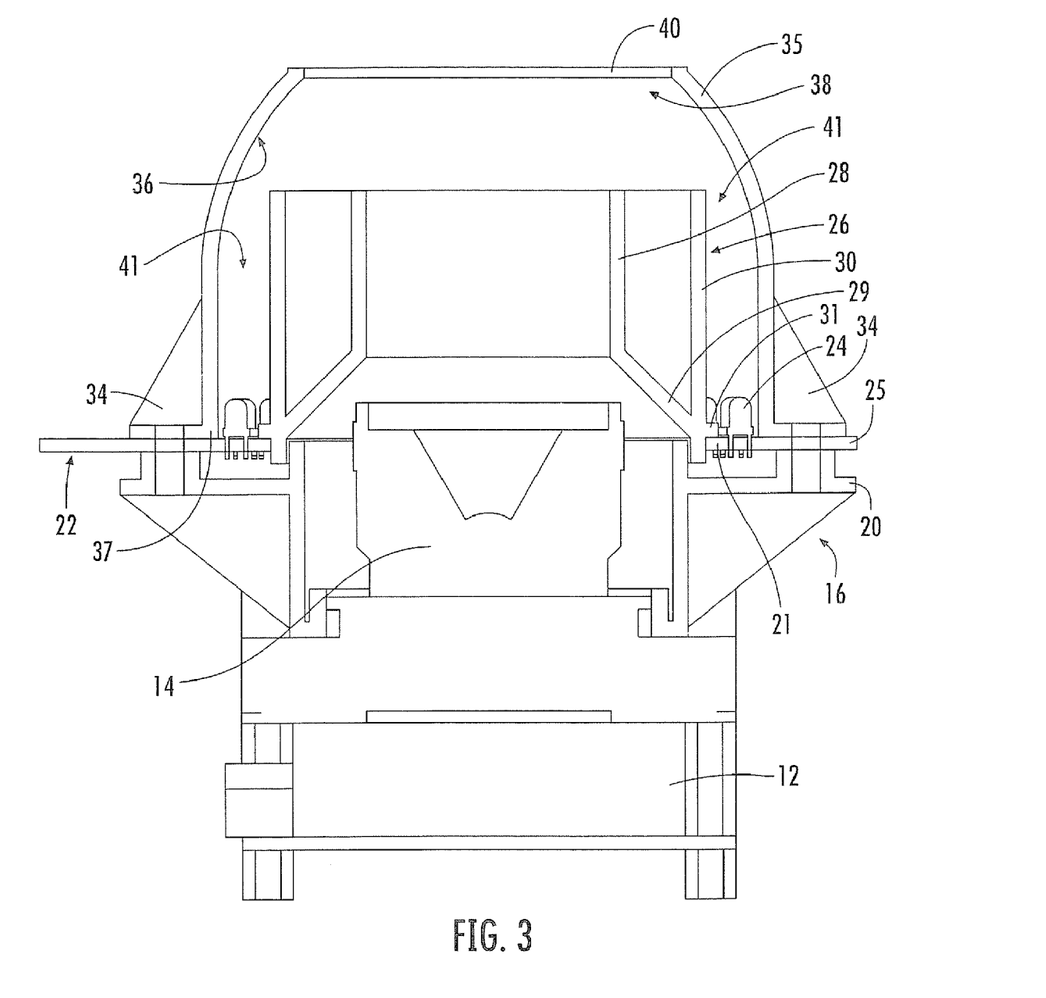
FIG. 3 is a section view of the components of FIG. 2 in an assembled form taken along lines 3-3 of FIG. 2.

Turning now to FIGS. 2 and 3, an imaging system for use in the vision station 124, designated broadly at 10, is shown therein. The system 10 includes a camera 12, a light ring 22, a light curtain 26, and a light dome 32. Each of these components is described in greater detail below.

The camera 12 can be any camera that is suitable for the acquisition of digital images. An exemplary camera 12 is Model No. Lw570C, available from Lumenera Corp., Ottawa, Canada. As shown in FIGS. 2 and 3, the camera 12 is mounted such that its lens 14 faces upwardly from its body 13. A sleeve 16 rests on the upper surface of the body 13 and circumferentially surrounds the lens 14. The sleeve 16 includes radially-extending tabs 18 that are used to mount the sleeve 16 to the camera 12, and also includes two flanges 20 that extend radially from diametrically opposed sections of the upper edge of the sleeve 16.

Referring still to FIGS. 2 and 3, the light ring 22 has a generally annular and planar body portion 21. Tabs 25 extend radially from diametrically opposed sections of the body portion 21 and are used to provide mounting locations for the light ring 22 on top of the sleeve 16. A series of light emitting diodes (LEDs) 24 are mounted on the upper surface of the body portion 21. The LEDs 24 may be alternating red/green/blue (RGB) LEDs that produce corresponding RGB wavelengths using a conventional RGB color scheme to produce white light. Alternatively, in some embodiments, LEDs 24 that produce white light may also be included. The LEDs 24 are adjustable in intensity, such that the intensity of red, green and/or blue light can be varied. As such, the color of light emanating from the light ring 22 can be adjusted as desired. Intensity and wavelength levels of red, green and blue light that can be employed to produce a particular shade of light are known to those of skill in this art and need not be detailed herein.

The light ring 22 also includes one or more infrared LEDs 27. The infrared LEDs 27 are adjustable in intensity. Typically, the infrared LEDs 27 are distributed relatively uniformly around the body portion 21 of the light ring 22.

With RGB LEDs 24 and infrared LEDs 27, the light ring 22 can allow independent control of the IR, red, green and blue light intensity (typically via pulse width modulation (PWM) or analog voltage). The light ring 22 can also be set up in a dependent mode where the intensity of all the LEDs can be changed together, but equally balanced.

Referring again to FIGS. 2 and 3, the light curtain 26 includes an annular inner wall 28 and a concentric outer wall 30. A beveled surface 29 (FIG. 3) joins the lower edges of the inner and outer walls 28, 30. A radial lip 31 extends outwardly from the outer wall 30 and rests on the inner edge of the body portion 21 of the light ring 22. This placement of the lip 31 positions the outer wall 30 radially inward of the LEDs 24. The inner wall 28 is positioned above and generally axially aligned with the lens 14 of the camera 12.

Still referring to FIGS. 2 and 3, the light dome 32 is generally bowl-shaped, with a dome wall 35 having an opening 38 in its upper portion and a perimeter 37 at its lower edge. A clear glass window 40 fills the opening 38. Flanges 34 (only one of which is shown in FIG. 2) extend radially outwardly from diametrically opposed sections of the lower edge of the dome wall 35 and align with the flanges 20 of the sleeve 16 and the tabs 25 of the light ring 22. Fasteners can be inserted through the flanges 34, the tabs 25 and the flanges 20 to fasten the light dome 32, the light ring 22, and the sleeve 16 together.

Referring now to FIG. 3, the inner surface 36 of the dome wall 35 and the outer wall 30 of the light curtain 26 form an annular gap 41 through which light from the LEDs 24 can pass. The dome wall 35 has sufficient curvature that the edges of the window 40 are radially inward of the upper edges of the outer wall 30; as a result, light from the LEDs 24 cannot shine directly onto the window 40. Also, the inner surface 36 is typically formed of an anti-glare material or treated with an anti-glare coating (such as a flat white paint) to reduce or minimize specular reflection and/or increase or maximize diffuse reflection.

Figure 4:
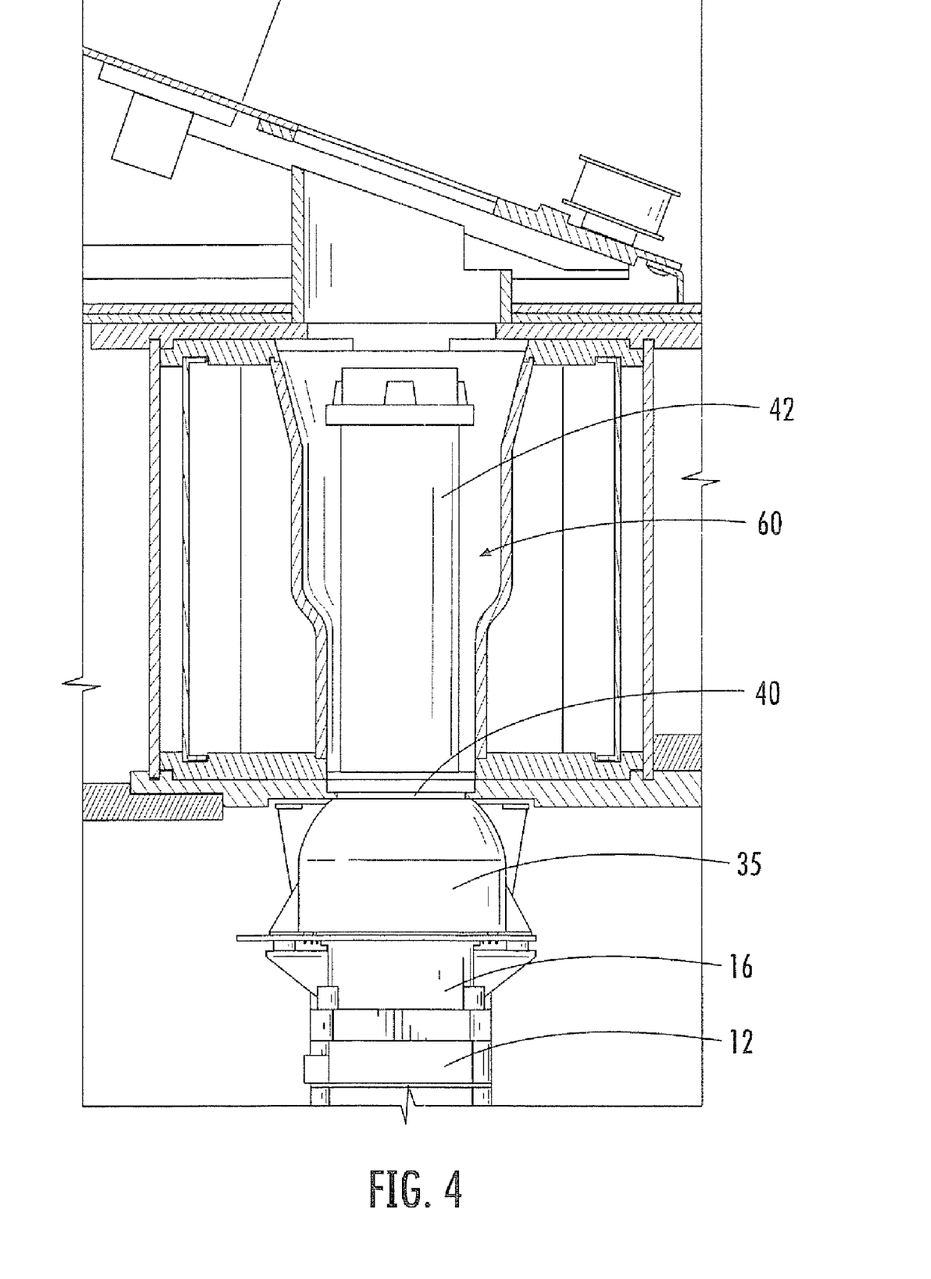
FIG. 4 is a section view of the vision system of FIG. 2 with a pharmaceutical vial residing therein.

Turning now to FIG. 4, the system 10 will ordinarily be employed with a chamber, such as chamber 60, in which resides the object (in this instance a pharmaceutical vial 42) for imaging. The chamber 60 is typically light-tight, such that the only appreciable light entering the chamber 60 enters through the window 40. In some embodiments, the chamber 60 will include a trap door or cover that allows the insertion of the object into the chamber but closes to prevent light from entering.

Referring back to FIG. 1, a controller 200 is connected to the camera 12 and the light ring 22. The controller 200 includes a memory 52 (either local or remote) that has stored image data for multiple pharmaceutical tablets. The controller 200 also has a processor 54 that enables data representing an image taken by the camera 12 to be compared to the stored image data to determine whether one or more visual features or attributes of the dispensed pharmaceutical match the visual features or attributes of a pharmaceutical stored in the memory 52.

In operation, as shown in FIG. 4 a vial 42 (typically a capped vial) containing a dispensed pharmaceutical is deposited in the chamber 60 and rests with its lower end on the window 40. The controller 200 activates the LEDs 24 of the light ring 22. Light from the LEDs 24 travels through the gap 41 to the inner surface 36 of the dome wall 35. However, because of the location of the outer wall 30 of the light curtain 26 and the position of the window 40, none of the light from the LED reaches the window 40 directly; instead, light reaching the window 40 (and, in turn, the vial 42 and the tablets residing therein) is indirect light, which produces little to no glare. This indirect light illuminates the vial 42 and tablets sufficiently for an image to be taken with the camera 12. In some embodiments, substantially all of the light reaching the window 40 is indirect light. The controller 200 then stores the image for subsequent processing, comparison to known image data, and/or other tasks.

It should be noted that, due to the adjustable nature of the LEDs 24 of the light ring 22, the color of light illuminating the vial 42 and tablets can be selected for advantageous imaging. For example, as discussed in co-pending and co-assigned U.S. patent application Ser. No. 12/249,402, filed Oct. 10, 2008, the disclosure of which is hereby incorporated herein by reference, images of tablets contained in a transparent amber-colored vial and acquired through the wall of the vial may exhibit substantially the same color as the tablets themselves when the vial is illuminated with light of a "reverse" or "tuned" color. As discussed in detail in the cited patent application, a "reverse" or "tuned" color is one that uses reciprocal values for red, green and blue in an RGB system as compared to an object, such as a pharmaceutical vial. The wavelength of a tuned color is one that passes through a material with selective transmittance (i.e., a medium that absorbs only certain wavelengths); it features an excess of energy in a particular range to make up for the net loss due to the medium's absorption. The use of light that is tuned to the color of a transparent amber vial (e.g., a bluish hue for an amber vial) can enable images of objects in the vial, wherein the images are acquired through the walls of the vial, to exhibit the same color as the objects would exhibit without the vial. Thus, the LEDs 24 of the light ring 22 can be adjusted to produce light having a tuned color to that of the vial (again, as an example, a bluish light for an amber-colored vial).

In one embodiment, the light color can be determined by first taking an image of the vial 42 with the camera 12. A histogram of that image can be produced. The inverse color of the histogram can then be determined, and the controller 200 can, through the LEDs 24 of the light ring 22, generate light of the inverse color.

In other embodiments, a sensor (not shown) may be included in the vision system 10 to detect the color of the vial 42. The sensor can transmit signals regarding the color of the vial 42 to the controller 200, which then induces the LEDs 24 of the light ring 22 to produce light of a "tuned" color to that of the vial 42. In such an embodiment, the system 10 can "tune" the light emitted from the LEDs 24 to account for differently-colored vials or variations in color due to different manufacturers, different lots, or the like.

Also, in some embodiments, the controller 200 may, in view of the identity of the prescribed pharmaceutical labeled on the vial (typically in bar code form), adjust the light produced by the LEDs 24 of the light ring 22 to a color that is particularly advantageous for distinguishing the prescribed pharmaceutical from a similar pharmaceutical. Thus, in those embodiments the color of the light may be one that is not substantially the reverse color of the vial, but is advantageous for detection of the particular pharmaceutical in the particular vial by most greatly enhancing the differences from the similar pharmaceutical.

Notably, the addition of IR light capability can provide significant performance enhancements. When the sample area is illuminated by IR light (used herein to be synonymous with infrared "radiation"), in a captured image the shapes of the pills within a vial can become much more defined and the contrast can be greater than when other wavelengths are employed. Also, the fact that at IR wavelengths materials have a response that is substantially unaffected by dyes (which instead respond predominantly in the visible range) enables IR light to provide suitable illumination for certain pills, such as multi-colored and dark pills, that often cannot easily be identified through software vision techniques based either on edge detection or thresholding of intensity because the pills are not robustly distinguishable from the background. There are some cases where IR lighting can be used to detect and locate objects that otherwise would appear substantially or completely invisible using visible light wavelengths. In addition, the penetrating properties of IR light can eliminate the effect of some surface features of pills, such as ink marking, which may interfere with machine vision by generating false edges.

The foregoing indicates that, by employing IR lighting either alone or in conjunction with visible light techniques, analysis of the shape of pills can be more accurate and/or reliable. The absorption of IR light also depends on the material the pills are made of, which may provide additional spectral information that can be exploited to assist in identifying the pills.

Further, illumination at one intensity (i.e., brightness) for one pill may saturate on a different pill or may provide inadequate illumination at a constant given exposure. Thus, it may be desirable in some embodiments for the intensity of the LEDs of the light ring (R, G, B, W, IR and/or even UV, were UV to be included) to be independently adjustable to either avoid saturation or provide increased illumination of certain pills.

Other light conditions can provide useful information; for instance, blue light is largely blocked/absorbed by the amber vials, so such illumination can highlight features belonging to the vial that should be removed in the image processing of pictures collected under other conditions.

Figure 5:
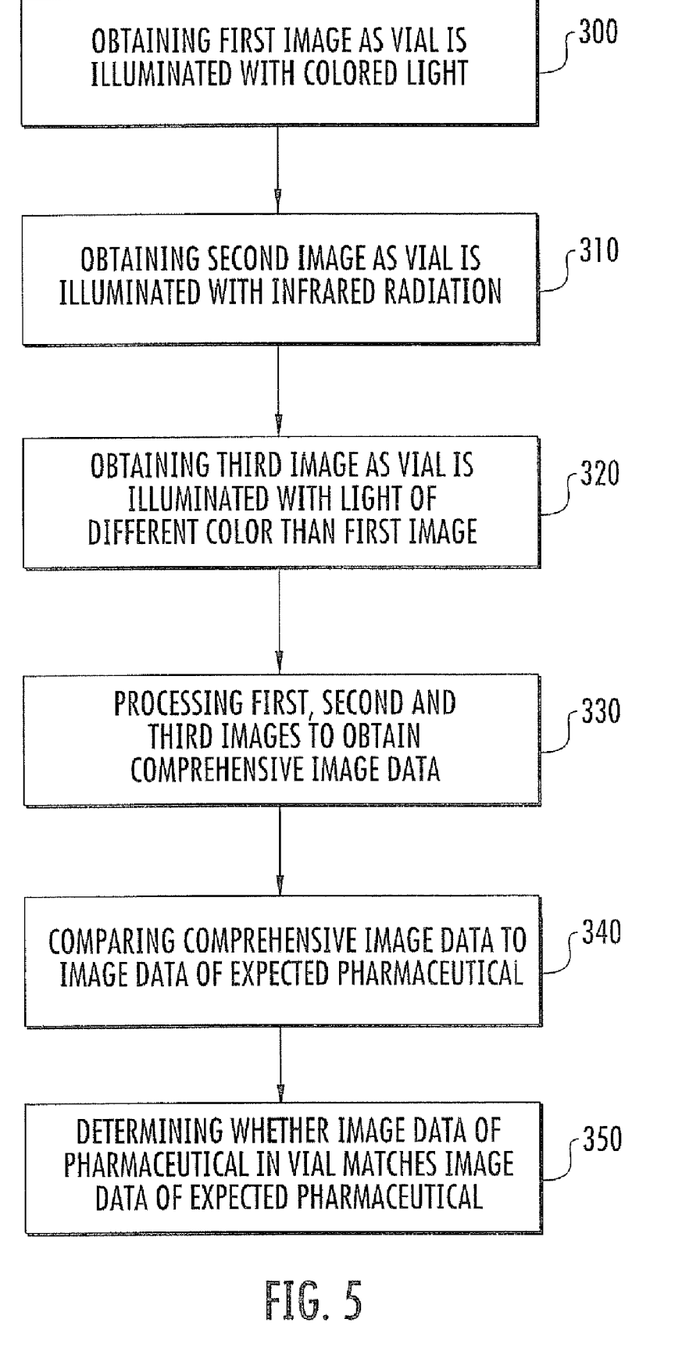
FIG. 5 is a flow chart describing operations associated with a method according to embodiments of the present invention.
Figure 6A:
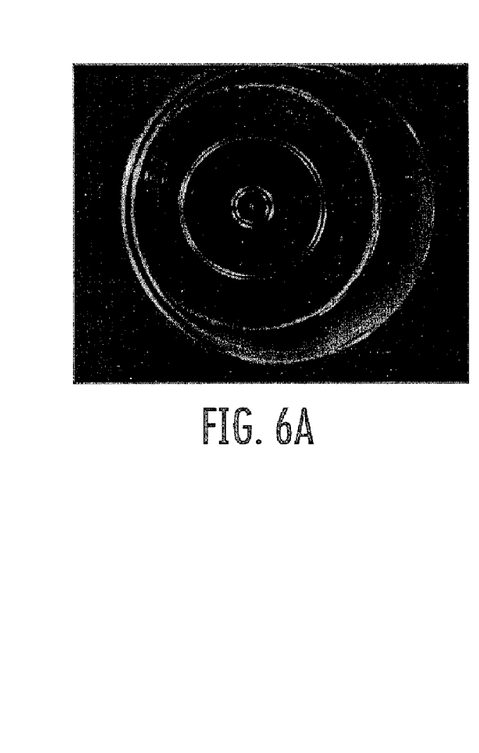
FIGS. 6A-6C, 7A-7C and 8A-8C are photographs of amber vials under different light conditions. In each group of images, images A, B and C were taken under blue, blue and white, and IR light respectively.
Figure 6B:
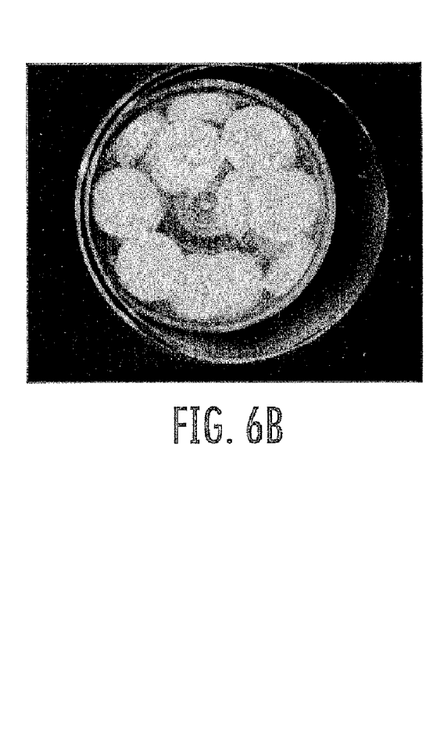
Figure 7A:
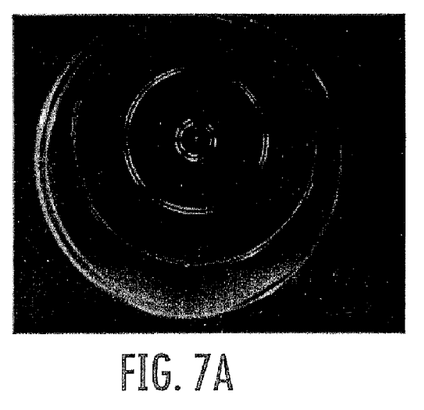
Figure 8A:
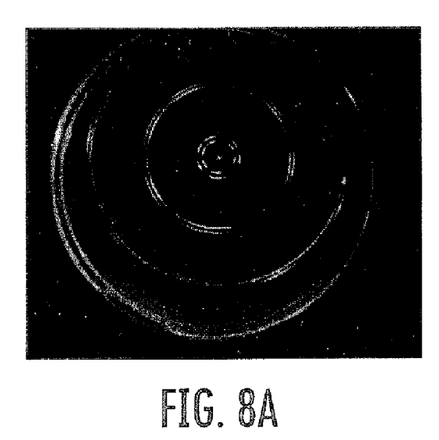

There are several potential advantages in using multiple light conditions in this system, since every light condition can enhance different aspects of the object. FIG. 5 illustrates an identification scheme according to embodiments of the present invention. As a vial is positioned in the chamber 60, the vial is illuminated with colored light, and a first image is obtained (Block 300). As used herein, "colored light" means non-white visible light, e.g., light produced by an intensity imbalance between red, green and blue components, and may include UV light in some embodiments. In many instances, the colored light will be blue (i.e., only the blue LEDs 24 are illuminated), which is largely blocked/absorbed by an amber vial; other color combinations of vial and light may also be employed. Particularly at low intensities, the blue light does not illuminate the pills inside the vial, but highlights the markings/artifacts on the bottom of the vial. This information can be used to identify regions of the image that are covered by vial features, especially when such regions are hard to isolate under other light conditions (see FIGS. 6A, 7A and 8A).

Figure 6C:
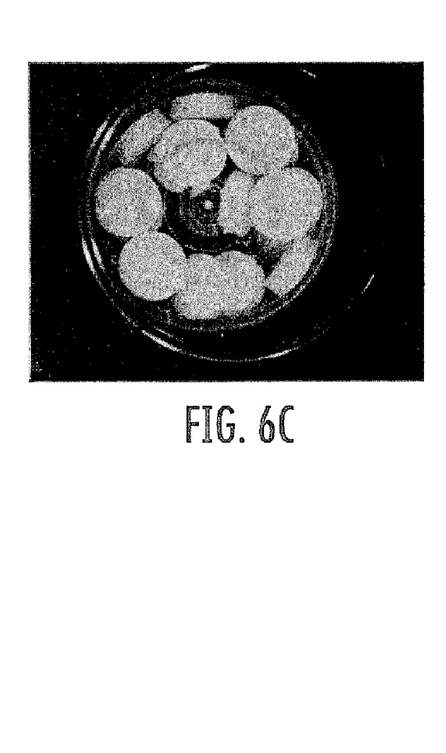
Figure 7B:
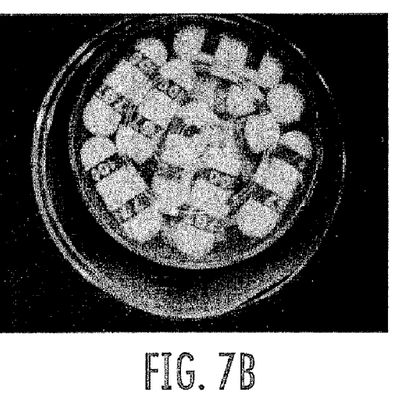
Figure 7C:
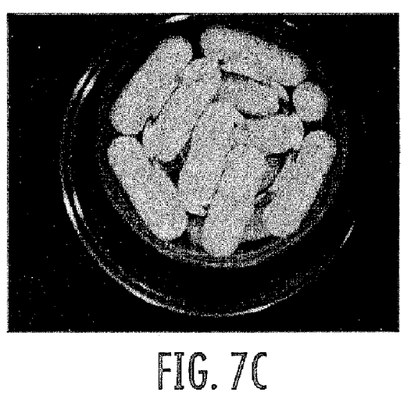
Figure 8B:
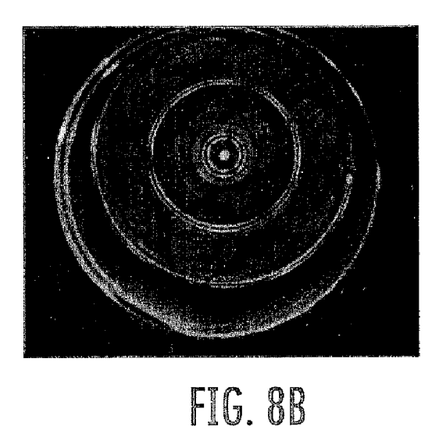
Figure 8C:
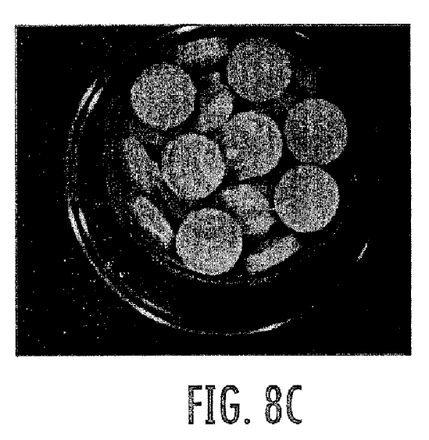

A second image is obtained as the vial is illuminated with infrared light (Block 310) from the IR LEDs 27. IR illumination can show the pills in the vial, since most typical vials are transparent to IR radiation; however, the pills appear largely featureless in terms of color, and the bottom of the vial can create a lenticular distortion that warps the shape of the pills (see FIGS. 6C, 7C and 8C). Nonetheless, an image taken under IR illumination can help to determine the location and/or position of one or more pills.

A third image can be obtained (Block 320) as the vial is illuminated with light that is a different color than the light employed at Block 300. Visible light alone can carry valuable color information, but the vial may generate objects in the scene that are not part of the pills and should not be considered. Also, dark pills may be hard to detect from the background. Multi-colored pills may generate false edges that may interfere with the detection of the pills (see FIGS. 68, 7B and 8B). The light used in some embodiments is a mixture of blue and white light, which can be generated either by illuminating the vial with equal amounts of red and green light and a greater amount of blue light (using the RGB LEDs 24), or with blue and white light (using the blue and white LEDs 24). In many embodiments, blue light used in this step differs from that employed in step 300 above, in that a much higher intensity of blue light is employed. In some embodiments, the blue light is at a sufficiently high intensity that enough of the blue light passes through the vial (despite a high percentage being blocked/absorbed by the vial) to produce light that is substantially white in the vial when the blue light that passes through the vial is combined with red and green light components. In some embodiments, the color of the light is substantially the "tuned" color of the vial, as discussed above, that substantially matches the absorbed wavelengths of the vial.

Data from the first, second and third images are then processed to produce comprehensive set of image data (Block 330). The first image (with colored light) can be used to calculate the position of the vial, for instance, by search of templates corresponding to the shape and size of the bottom of the vial. Also, regions of the images that contain vial features can be located, for instance, by examining the intensity levels of the reflected blue light, and then removed. The second image (with IR) can be used to determine the location of the pills within in the vial. As an example, common edge detection algorithms (e.g., LaPlacian operation of Gaussian edge detectors) along with pill features (size, shape, area, etc.) may be employed. The third image (with a differently colored, often tuned, light) can then be used to calculate features of the image in the regions known to contain pills from the IR image; for example, the statistical distribution of the color hues may be determined.

The comprehensive data set is then compared to image data for the pharmaceutical expected to be in the vial (Block 340). This comparison can be performed in a number of ways, and is described in detail in U.S. patent application Ser. No. 12/623,822, filed Nov. 23, 2009, the disclosure of which is hereby incorporated herein in its entirety. Typically, the pharmaceutical expected to be present in the vial is identified via a bar code, RFID tag or the like on the vial (for example, the scanning station 122 of the system 120 can read a bar code on a vial). The comparison permits a determination by the controller 200 of whether the image data of the pharmaceutical in the vial matches the image data of the expected pharmaceutical (Block 350). This comparison may be performed in a number of ways, including those described in application Ser. No. 12/623,822, supra.

Figure 9:
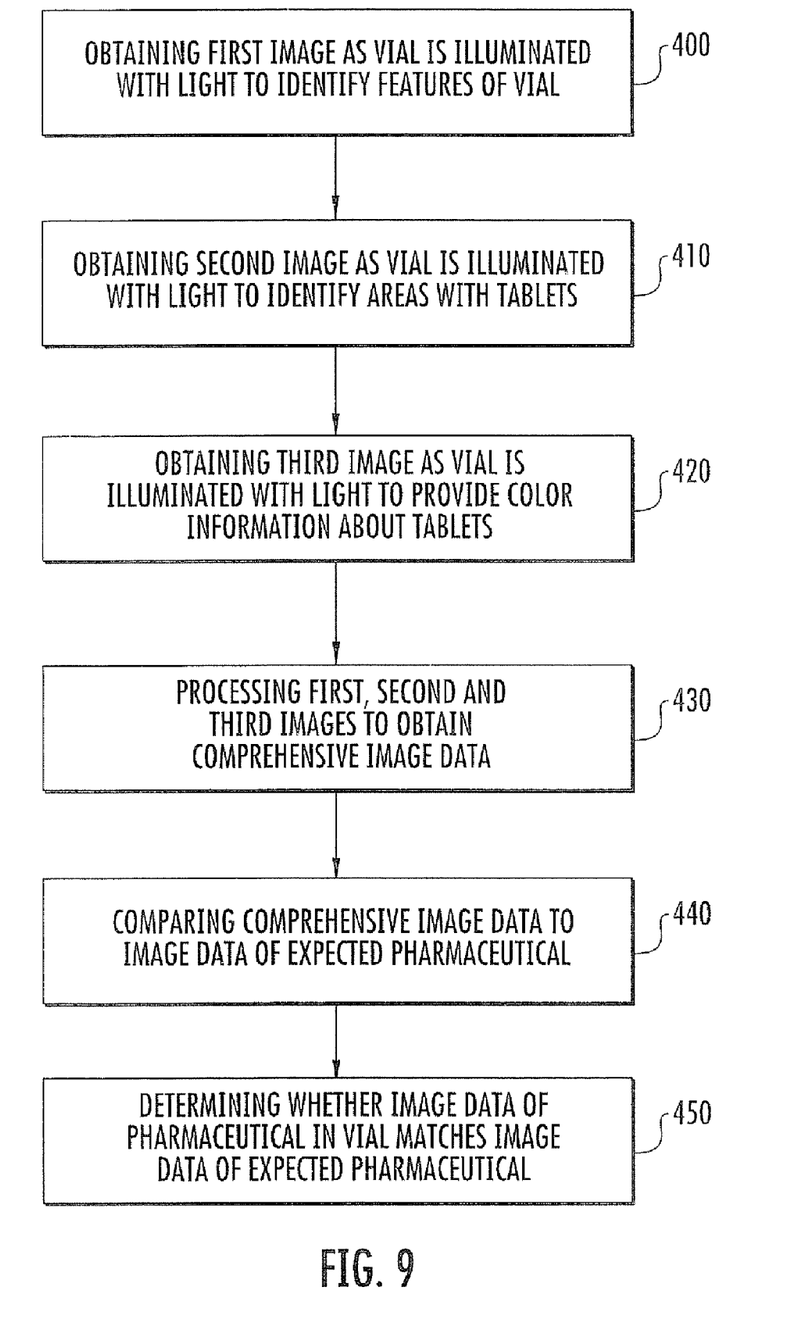
FIG. 9 is a flow chart describing operations associated with a method according to embodiments of the present invention.

An alternative method according to embodiments of the invention is illustrated in FIG. 9. The method includes as a first step obtaining a first image of the vial as it is illuminated with light selected to identify features of the vial (Block 400), such as colored light as described above. A second image of the vial is obtained as it is illuminated with light, such as IR, that is selected to identify regions that contain tablets (Block 410). A third image of the vial is obtained as it is illuminated with light that is selected to provide color information about the tablets (Block 420); such light may be a color that is tuned to the color of the vial. The first, second and third images are processed to obtain comprehensive image data (Block 430). The comprehensive image data is compared to image data of a known pharmaceutical expected to be contained in the vial (Block 440). A determination is then made regarding whether the pharmaceutical in the vial is the expected pharmaceutical based on the comparing step (Block 450).

Those skilled in this art will recognize that the information/data gathered in any or all of these exemplary steps can be analyzed and processed by other known image processing and comparison techniques. Exemplary techniques are described in U.S. Pat. No. 6,535,637 to Wootton et al. and U.S. patent application Ser. No. 12/623,822, filed Nov. 23, 2009, the disclosures of which are hereby incorporated herein by reference. In addition, those skilled in this art will appreciate that the steps of obtaining the images may be performed in any sequence. In fact, in some embodiments the steps of illuminating a vial with colored light may be combined into a single step, in which the light is selected to identify features of the vial and to provide color information about the tablets.

The foregoing is illustrative of the present invention and is not to be construed as limiting thereof. Although exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention.

That which is claimed is:

1. A method of determining the identity of pharmaceutical tablets contained within a pharmaceutical vial, comprising the steps of:

obtaining a first image of the vial as it is illuminated with colored light;

obtaining a second image of the vial as it is illuminated with infrared radiation;

processing the first and second images to obtain comprehensive image data;

comparing the comprehensive image data to image data of a known pharmaceutical expected to be contained in the vial; and determining whether the pharmaceutical in the vial is the expected pharmaceutical based on the comparing step.

2. The method defined in claim 1, wherein the colored light is blue.

3. The method defined in claim 2, wherein the processing step comprises removing vial artifacts from the comprehensive image data based on data from the first image.

4. The method defined in claim 1, wherein the processing step comprises locating the position of one or more of the pharmaceutical tablets based on data from the second image.

5. The method defined in claim 1, further comprising the step of obtaining a third image of the vial as it is illuminated with light that is a different color than the colored light employed in obtaining the first image;

wherein the processing step comprises processing the first, second and third images to obtain comprehensive image data.

6. The method defined in claim 5, wherein the color of light employed in obtaining the first image is substantially the reverse color of the vial.

7. The method defined in claim 1, wherein the vial has an amber hue.

8. A method of determining the identity of pharmaceutical tablets contained within a pharmaceutical vial, comprising the steps of:

obtaining a first image of the vial as it is illuminated with colored light;

obtaining a second image of the vial as it is illuminated with infrared radiation;

obtaining a third image of the vial as it is illuminated with light of a color that is a different color than the light employed in obtaining the first image;

processing the first, second and third images to obtain comprehensive image data;

comparing the comprehensive image data to image data of a known pharmaceutical expected to be contained in the vial; and determining whether the pharmaceutical in the vial is the expected pharmaceutical based on the comparing step.

9. The method defined in claim 8, wherein the colored light employed to obtain the first image has a bluish hue.

10. The method defined in claim 9, wherein the processing step comprises removing vial artifacts based on data from the first image, and determining the position of one or more tablets based on data from the second image.

11. The method defined in claim 10, wherein the processing step comprises determining the color of one or more pharmaceutical tablets based on data from the third image.

12. A method of determining the identity of pharmaceutical tablets contained within a pharmaceutical vial, comprising the steps of:

obtaining a first image of the vial as it is illuminated with light selected to identify features of the vial;

obtaining a second image of the vial as it is illuminated with light selected to identify regions that contain tablets;

obtaining a third image of the vial as it is illuminated with light that is selected to provide color information about the tablets;

processing the first, second and third images to obtain comprehensive image data;

comparing the comprehensive image data to image data of a known pharmaceutical expected to be contained in the vial; and determining whether the pharmaceutical in the vial is the expected pharmaceutical based on the comparing step.

13. A method of determining the identity of pharmaceutical tablets contained within a pharmaceutical vial, comprising the steps of:

obtaining a first image of the vial as it is illuminated with light selected to identify features of the vial and to provide color information about the tablets;

obtaining a second image of the vial as it is illuminated with light selected to identify regions that contain tablets;

processing the first and second images to obtain comprehensive image data;

comparing the comprehensive image data to image data of a known pharmaceutical expected to be contained in the vial; and determining whether the pharmaceutical in the vial is the expected pharmaceutical based on the comparing step.

* * * * *